(12) United States Patent
Franzen

(10) Patent No.: US 6,770,443 B2
(45) Date of Patent: Aug. 3, 2004

(54) METHOD AND APPARATUS FOR MASS SPECTROMETRIC GENOTYPING

(75) Inventor: Jochen Franzen, Bremen (DE)

(73) Assignee: Bruker Daltonik GmbH (DE)

( * ) Notice: Subject to any disclaimer, the term of this patent is extended or adjusted under 35 U.S.C. 154(b) by 0 days.

(21) Appl. No.: 10/099,157

(22) Filed: Mar. 15, 2002

(65) Prior Publication Data
US 2002/0146735 A1 Oct. 10, 2002

(30) Foreign Application Priority Data
Mar. 15, 2001 (DE) .......................... 101 12 387

(51) Int. Cl.$^7$ ............. C12Q 1/68; C12N 15/00; C12N 15/63; C12N 1/20; C07H 21/04
(52) U.S. Cl. ............. 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1
(58) Field of Search .............. 435/6, 91.1, 91.2; 536/24.3; 935/6; 436/518

(56) References Cited

U.S. PATENT DOCUMENTS

| | | | |
|---|---|---|---|
| 5,874,219 A | | 2/1999 | Rava et al. |
| 5,885,775 A | | 3/1999 | Haff et al. |
| 6,024,925 A | * | 2/2000 | Little et al. ............. 422/100 |
| 6,090,558 A | | 7/2000 | Butler et al. |
| 6,194,563 B1 | * | 2/2001 | Cruickshank ............. 536/25.3 |
| 6,454,924 B2 | * | 9/2002 | Jedrzejewski et al. ...... 204/601 |
| 2002/0048765 A1 | | 4/2002 | Shao et al. |

FOREIGN PATENT DOCUMENTS

| | | | |
|---|---|---|---|
| DE | 33 35 581 A1 | 4/1985 | |
| DE | 197 54 978 A1 | 7/1999 | |
| DE | 198 24 280 A1 | 12/1999 | |
| DE | 198 52 167 A1 | 5/2000 | |
| DE | 101 08 453 A1 | 9/2002 | |
| WO | WO 07/27325 | * 7/1997 | ............. 422/100 |

OTHER PUBLICATIONS

Ravine, D., "Automated mutation analysis", J. Inher. Metab Dis., Dis., vol. 22, 1999, pp. 503–518, Netherlands.

* cited by examiner

Primary Examiner—Jeffrey Fredman
Assistant Examiner—Arun Chakrabarti

(57) ABSTRACT

Methods and equipment are provided for the mass spectrometric measurement of a large number of genotyping profiles, each formed by several tens to several hundreds of SNPs (single nucleotide polymorphisms). A multitude of chips each carrying an array of surface-bound oligonucleotide probes for mutations are synchronously processed. The chips are attached to plates such that they can be immersed in a multitude of wells with DNA samples requiring analysis while also serving directly as sample carriers in mass spectrometers. The multitude of wells can, for instance, take the form of microtitre plates. Primers may be used which possess a photolytically or chemically cleavable linker that bridges one base pair and does not hinder either the possibility of hybridization or enzymatic extension. Light or chemicals can then be used to cleave short chains particularly suitable for ionization by matrix assisted laser desorption and mass spectrometric analysis using time-of-flight mass spectrometers.

20 Claims, 1 Drawing Sheet

METHOD AND APPARATUS FOR MASS SPECTROMETRIC GENOTYPING

FIELD OF THE INVENTION

The invention concerns methods and equipment for the mass spectrometric measurement of a large number of genotyping profiles, each formed by many SNPs (single nucleotide polymorphisms) in a DNA sample, and for the associated sample preparation.

BACKGROUND OF THE INVENTION

There is a growing demand for easy, fast and economical generation of specified genotyping profiles, each involving the determination of many SNPs in a DNA sample, partially up to several tens or even to several hundreds of SNPs. Such a profile can, for instance, identify a person or an animal, to provide evidence for the responsibility for a crime, or to exclude fraudulent substitutions (for example, in the case of race horses, cattle, pedigree dogs or pigeons). With about 50 SNPs a person can be uniquely identified from a tiny sample of DNA. This kind of profile can also provide evidence of ancestry, as proof of paternity, or as proof of the pedigree of cattle.

A particularly important use of genotype profiles, however, is the preventive detection of predispositions to disease, for instance a tendency towards thrombosis, or for the purposes of individualized medication (the "personal pill"). It is to be expected that the measurement of such genotype profiles with high analytic reliability will play an important role in the medicine of the future. The analytic reliability required for this can, to date, only be guaranteed by mass spectrometry.

Thus the field of this invention is a method for the detection of a large number of specific mutational changes in the genomic DNA in the course of a single, easy analysis process, where the mutation sites themselves are known and are specified for the genotyping task. As far as the mutational sequence changes are concerned, particular attention is paid to the simple exchange of bases ("point mutation"), which has become known recently under the abbreviation "SNP" (single nucleotide polymorphism). For human beings it is believed that at least three million SNPs occur frequently, which characterize many of the individual differences between people and control the individual genetic predisposition.

Usually a "wild type" is defined for a genome, and this "wild type" is considered to be free from mutations. Bearing in mind the frequency of mutations, for instance of SNPs, and the equal validity of the mutated type (mutants) and of the wild type, the definition of the wild type is arbitrary, or at least a matter of chance.

All the mutations of DNA considered here result in a difference in the mass of the segment of DNA containing this mutation as compared with the mass of the corresponding section from the wild type. This means that precise determination of the mass of a segment of DNA can be used to determine a mutation.

Mass spectrometry is an extremely powerful method for measuring the masses of biomolecules. The mass of the ions can be analyzed by mass spectrometry, for instance in time-of-flight mass spectrometers using ionization by matrix assisted laser desorption (MALDI). But ionization by electrospray ionization (ESI) can also be used, although usually in association with mass spectrometers of a different type.

Polymerase chain reactions (PCR) can be used to manufacture selected double-strand DNA products with a minimum length of about 40 base pairs by application of a pair of "selection primers", single-strand oligonucleotides with a length of about 20 bases, in a known manner. The mutation site must be included by corresponding selection of the sequence of the two selection primers.

The obvious process of using mass spectrometry is simply to measure the mass of DNA products multiplied by PCR and so to determine the mutations. This process has been found almost impossible to implement, because accurate measurement of the masses of DNA products with lengths of more than 40 base pairs has proved impossible in practice. The reasons for this are given below.

Methods have therefore been sought that yield shorter DNA fragments. For this purpose, the process of limited, mutation-dependent primer extension was first developed, which generates extended primers having a length of about 15 or 25 nucleotides, from whose mass the type of mutation can be determined more effectively. Other improvements consist in the removal of a large piece of this extended primer, for instance by enzymatic digestion of a piece; the details of this will not be described any more closely here.

The invention of photo-cleavable linkers brought further progress. The linkers are integrated into the extension primers, and bridge one nucleotide without disturbing either the hybridization or the enzymatic extension, and can be cleaved by means of UV light following preparation of the sample. This allows small fragments with lengths of only 4, 5 or 6 nucleotides to be obtained, and these can be very effectively ionized using matrix assisted laser desorption and ionization (MALDI).

The MALDI preparation and measurement procedure consists in first embedding the analyte molecules on a sample carrier in a solid, UV-absorbing matrix, usually an organic acid. The sample carrier is inserted into the ion source of a mass spectrometer. A short laser pulse, about three nanoseconds in duration, is used to vaporize the matrix into the vacuum; during this process the analyte molecules are transported into the gaseous phase largely, though unfortunately not completely, unfragmented. The molecules of analyte are ionized by proton transfer as a result of impacts with matrix ions that are created at the same time. An applied voltage accelerates the ions into a field-free flight tube. Because of their different masses, the ions are accelerated in the ion source to different velocities. Smaller ions reach the detector earlier than larger ions. The measured flight time is used to calculate the masses of the ions.

MALDI is particularly suitable for the analysis of peptides and proteins. The analysis of nucleic acid chains is more difficult, and is only adequately effective for short-chain nucleic acids. The reason for this is that only a single proton needs to be captured to ionize peptides or proteins to form a positive ion, whereas nucleic acids form a poly-anion with multiple negative charges at the sugar phosphate backbone (one negative charge for each nucleotide), and the ionization process to form a positive ion is significantly less efficient because it needs the transfer of a multitude of protons from a multitude of matrix ions. It is only of adequate efficiency for very short chains, such as for the cleavage products of the extended primers, as can be created with the aid of photo-cleavable linkers.

It is a well-known and favorable embodiment for the analysis of genotyping profiles of DNA samples to use chips on which sufficient numbers of different types of extension primers are bonded in separate locations as probes for the selected SNPs of the genotyping profile. In association with the use of cleavable primers, as discussed above, this therefore provides a powerful tool for the mass spectrometric analysis of genotyping profiles.

SUMMARY OF THE INVENTION

The invention consists of providing a multitude of chips held simultaneously in a combining structure, as well for the sample preparation in a matching multitude of processing wells and as for the joint mass spectrometric analysis for the determination of numerous genotyping profiles. For this purpose the chips are held by the combining structure in such a way that they can be fed as a rigid unit to the multitude of wells with DNA samples as well as to the mass spectrometric analysis. The multitude of wells can, for instance, be a microtitre plate.

The combining structure can be a flat plate containing the chips as parts of its surface and which is pressed closely onto the processing wells, such as the wells of a microtitre plate, so that it comes into contact with the liquid inside the wells when the structure with the processing wells is inverted.

The linking structure is, however, preferably a plate on which the chips sit rigidly on small stems or pillars, so that when this chip carrier plate is turned over the chips can be immersed simultaneously in the wells, for instance in the wells of a microtitre plate, at the same time closing the wells.

Both types of carrier plates may—as they stand, or with an additional frame—be inserted into the mass spectrometer. An electrically conducting top frame is particularly necessary for the chip carrier plate in which the chips are on stems, so that the electrical potential gaps between the chips are filled and the chips may be electrically contacted for use in the mass spectrometer. It is favorable for the acceleration of the ions created on the chips by pulsed laser desorption to originate from a wide and even plane with identical electrical potential throughout the plane.

In order for the chips to be properly positioned in the top frame for mass spectrometric analysis and accurately located in one plane, it is expedient to make the stems of the chips elastic, and for the chips to be precisely shaped so that they fit positively into the corresponding negative shapes in the top frame. The top frame will then provide very precise adjustment to the chips, both laterally and in reference to the plane.

Each of the chips carries the oligonucleotide probes that have to be provided with the chip for processing and prepared for mass spectrometric analysis. These probes are bonded to the surface in a large number of compartments. One known processing method is limited mutation-dependent primer extension, in which the oligonucleotides are extended enzymatically by precisely one nucleotide after the deposition of template strands that carry the mutation. The nucleotide used for the extension thus carries the information about the mutation. It is very expedient for the oligonucleotides to carry a cleavable linker not far from the 3' end that can be cleave after the processing, and supplies uniformly short fragments, for instance only 5 nucleotides in length, which carry the mutation information and can easily be measured by mass spectrometry.

In order to detect and compensate for the residual differences in the height of the chips within the potential plane, it is expedient to have reference signals with precisely known mass in the spectrum of each compartment. These are helpful for determination of the mass, because the flight times of MALDI ions are shifted as the separation from the nearest acceleration electrode varies. These mass references can easily be added to the individual compartments when the chips are manufactured. They consist of reference primers with terminating ends, and also having cleavable linkers. These are not extended, but supply cleavage products with precisely known masses. It appears that even one such reference primer in each compartment is sufficient, although two reference primers for each compartment, located as close as possible to the ends of the range of masses, are better.

A further idea of the invention is to provide a ready made application kit for the determination of a genotyping profile, containing at least the chip carrier plates with chips, each having the oligonucleotide probes for complete genotyping and the necessary primer pairs for multiplex PCR amplification of the DNA sample for manufacture of the template.

It is also possible for a package to additionally contain the NTPs for the amplifying PCR process, the cleaning media, the mixture of terminating ddNTPs and the data relating to the masses of the cleave segments to be expected in each compartment on a computer readable medium. It is even possible to include an executable computer program that calculates the medical, breeding or other relevant results according to the latest state of knowledge from the measured genotyping profile. It is furthermore possible to include the most favorable polymerases for the primary PCR amplification of the templates and for the primer extension and purified matrix substances for the MALDI ionization.

For urgent analyses it can be appropriate to have chip carrier plates with smaller numbers of chips available. This will shorten the measurement time in the mass spectrometer. Thus a carrier plate with 12 chips, at a measurement time of 1 second per compartment, can be measured in half-an-hour, whereas the measurement of a carrier plate with 96 chips takes four hours, and in any event is only possible with the most modern mass spectrometers. The time for preparation of the samples, however, is only shortened slightly.

DETAILED DESCRIPTION

Figure 1:
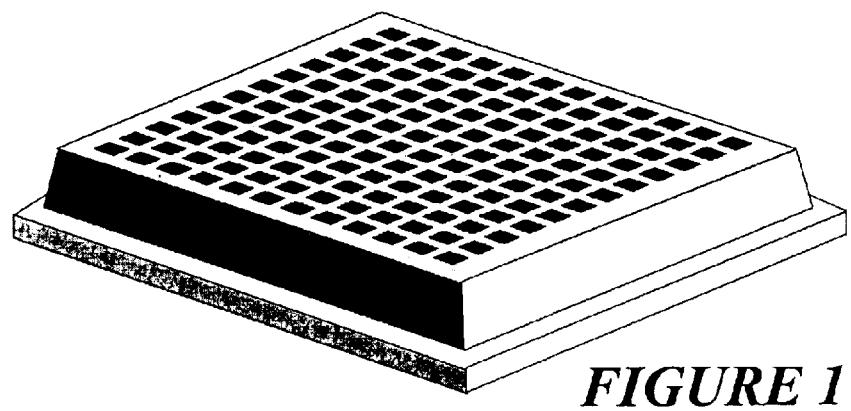
FIG. 1 shows a single chip (highly magnified) with the compartments that carry the oligonucleotide probes for the mutations of the genotyping profile. The chip has a shape which ensures easy insertion and effective adjustment in a top frame.
Figure 2:
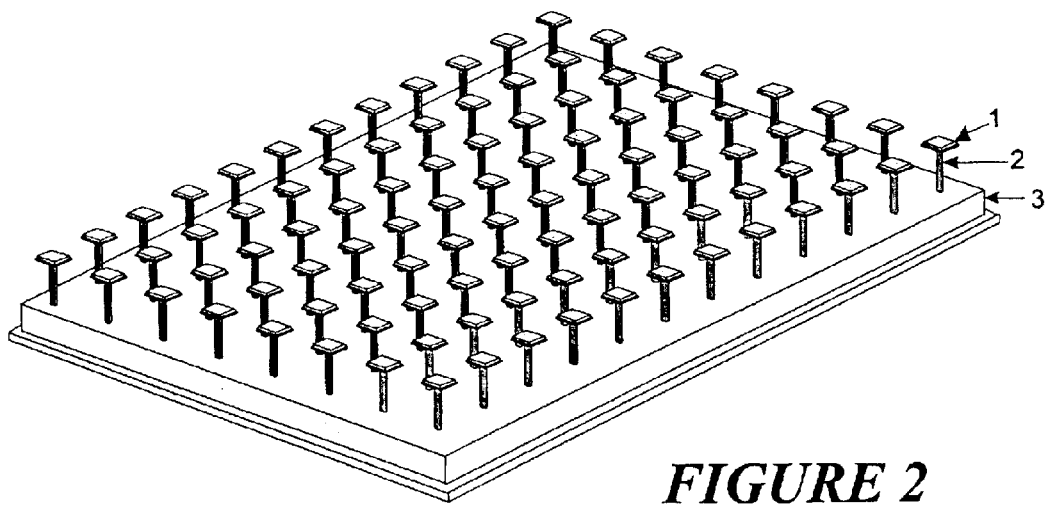
FIG. 2 shows a chip carrier plate in accordance with the invention. 96 chips (1) are located on slightly elastic stems (2), holding them in a grid on a base plate (3). The grid spacing corresponds to that of the wells in which the oligonucleotide probes on the chips are to be processed, which here is the spacing of a microtitre plate with 96 compartments.
Figure 3:
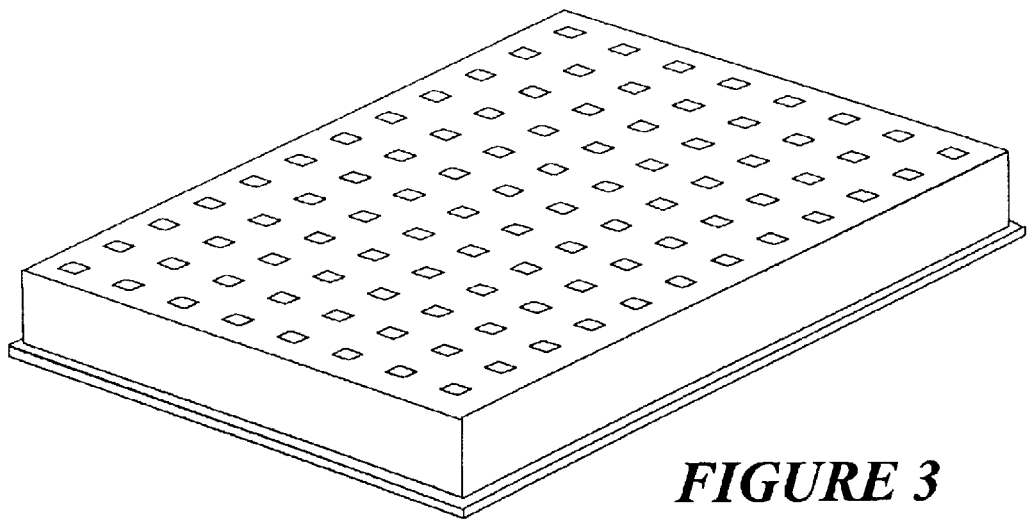
FIG. 3 shows the chip carrier plate inserted into an electrically conductive top frame that provides a potential plane and makes the contact to the chip for mass spectrometric analysis. The top frame can be the size and shape of a microtitre plate.

The analytic task addressed here is the easy, fast and economical generation of specified genotyping profiles represented by several tens to several hundreds of SNPs, each from a number of DNA samples.

The invention is used for the simultaneous preparation of samples for mass spectrometric measurement of many genotyping profiles, each of which is given by a relatively large number of mutations, primarily point mutations. The point mutations are frequently referred to as SNPs (SNP=single nucleotide polymorphism).

Particular reference is made here to the chip carrier plate in accordance with the invention, which carries the chips with the oligonucleotide compartments on stems, so that the chips can be submerged in the wells of a microtitre plate by inverting the chip carrier plate. This restriction, however, is not a restriction of the idea of the invention.

In the following, a method and associated equipment is described which measures the genotyping profile from 288 SNPs of a DNA sample with extremely high analytic reliability, while also saving time and being easy to carry out. This number of SNPs, and the particular details of the procedure are only used here as an example, since conversion to other numbers and slightly altered methods would be easy for a specialist in this field with knowledge of this invention.

The DNA sample is first prepared for a multiplex polymerase chain reaction (PCR), through the addition of 288 primer pairs as well as a solution of polymerase, the four dNTPs (deoxynucleoside triphosphates) and buffers. The primer pairs are selected in such a way that they all satisfy the same PCR conditions for successful amplification; nowadays computer programs are available that can successfully make this choice. Each primer pair creates a DNA segment that includes an SNP mutation site. The PCR product should have a length of about 60 to 100 nucleotides.

The amplification by the known thermocycles of the PCR thus yields a double-stranded PCR product for each of the selected SNPs, carrying the characterizing SNP site not far from its center. Following the amplification, many billions of each of these PCR products are present. These PCR products are then washed to purify them of any additives, adsorptively bound, for instance, to small magnetic spheres. Solutions containing such magnetic spheres for cleaning oligonucleotides are available commercially. Following the washing process, polymerase, buffer and NTPs are added again to the now detached PCR products for limited primer extension. This time, the NTPs involved are terminating dideoxynucleoside triphosphates (ddNTPs) which, when they bond to the extension primer, prevent any further extension, so that the extension is terminated.

All these processes are carried out in so-called microtitre plates (MTPs). These may have, for instance, 96 individual wells in a nine millimeter grid in a plate of standardized design, measuring about eight by twelve centimeters.

Chips carrying the array of the extension primers are now introduced to these wells, and the further sample preparation, up to the mass spectrometric analysis, takes place on these chips.

In one embodiment, the chips are about 3.5 by 3.5 mm in size, and on an array of 3 by 3 mm have a total of 144 compartments. Each square compartment has an edge length of 200 micrometers, and between the compartments there are hydrophobic separating tracks, 50 micrometers wide. Each of the nine square millimeters of the total array thus contains 16 compartments.

For one multiplex analysis for four SNPs, each compartment of the array is now occupied by a total of four different extension primers. The extension primers are chosen in such a way that they can hybridize with their 3' end immediately next to a mutation site of one of the single strands of DNA obtained from the double strand segments of the PCR products. Two extension primers are provided in our example for each DNA double strand segment: one for each of the two single strands. These two primers independently analyse each individual mutation; this internal cross-check provides an exceptionally high analytic reliability, similar to the double determination that is usual in medicine. In this way, the 144 compartments of one chip allow the analysis of a genotype profile from 288 SNPs with very high analytic reliability.

These primers are bound to the surface of the chip at their 5' end via an elastic bridge. They are usually about 20 nucleotides in length, but they carry a photo-cleavable linker exactly four nucleotides from their 3' end. This linker bridges precisely one nucleotide, and disturbs neither the hybridization nor the enzymatic extension through specially applied polymerase. A photo-cleavable linker is used here, cleavable by UV light, but more generally a linker that can be cleaved chemically could also be used.

The 96 chips for the analysis of a genotyping profile from the 96 DNA samples of a microtitre plate are, in our case, a particularly favorable embodiment of this invention on a carrier plate that has the size of a microtitre plate to which they are attached by small stems. The distance between the pillars corresponds exactly to the grid of the wells on the microtitre plate. The 96 chips can easily be immersed in the 96 sample solutions and processed there by inverting the carrier plate. This involves the carrier plate being shaped so that it seals all the wells on the microtitre plate. The 96 sample solutions contain, in particular, the mutation-bearing templates for hybridization on the oligonucleotide probes. The carrier plate with the 96 chips on the small pillars can then, after processing, be used directly as the sample plate for the mass spectrometer. For this purpose, a metal or metallized frame can be used in order to create the necessary even electrical accelerating voltage around the chips.

The extension primers used as mutation probes can be bonded to the compartments of the array on the chip surface when the chip is manufactured in a number of known ways. For example, a streptavidin-biotin bond can be used, which is formed automatically when solutions with biotinylizing primers is pipetted onto a surface covered with streptavidin.

The cleavable linkers are integrated, as bridges between two nucleotides, into the extension primers when they are created. They must bridge one nucleotide relatively precisely, and must appear similar to a nucleotide to the polymerase. Materials from the o-nitrobenzyl derivative class of bonds can be used in particular as the photo-cleavable linker.

It is favorable if the primers all can be cleaved at the same distance from the 3' end, because this creates cleavage fragments of the same length (counted in nucleotides) which have practically the same MALDI sensitivity and thus generate mass spectrometric signals of the same intensity. The most favorable length for the cleavage products is five nucleotides, which requires a cleavable bridge in the fifth position from the 3' end of the unextended primer. The range of masses for cleavage fragments of five nucleotides is around 1600 to 1800. The mass of the cleaving residue left behind by the linker on the cleavage product is added to the sum of the masses of the nucleotides.

A multiplexed analysis can, of course, also take place in every compartment of the array on the chip. This requires several types of extension primer to be bonded there in a uniform mixture. The extension primers of the SNPs must be selected here in such a way that the range of masses of the individual cleavage fragments do not have any interfering overlaps. Since each cleavage fragment only supplies one or two ion signals (just one signal each for homozygote A or B, two signals for the heterozygotic case), distributed over a mass range of 200 atomic mass units, this restriction is not very serious. Multiplex analyses for 2 to 10 SNPs in each compartment are easily possible.

The mass spectrometer does not have to have a high mass resolution. A resolution of about m/m=R=600 is sufficient; the isotope pattern from two or three individual signal signals separated by one mass unit each will not thereby be resolved, but will be effectively smoothed. The signals smoothed in this way make the measurement of masses to an accuracy of one or two atomic units quite possible. That is sufficient for the analytic task, because the distance between the two homozygotic signals, whose masses are to be distinguished, is at least 9 mass units.

It is, however, helpful to have reference signals with precisely known masses in the spectrum. These provide assistance in determining the mass, because the flight times of MALDI ions are often jointly shifted for very different reasons. These mass references can easily be added to the individual compartments when the chips are manufactured. They consist of reference primers with terminating ends, also having cleavable linkers. These are not extended, but do supply cleavage fragments with precisely known masses. Even one such reference primer in each compartment appears to be sufficient, but two reference primers in each compartment are better, as near as possible to the ends of the range of masses.

A total of four kinds of reference primers is sufficient for the manufacture of the chips: a substitute reference primer can be used at each end of the range of masses if it appears possible that a reference primer will overlap an analytic signal. The masses of the expected analytic signals are in this case known in advance.

In another embodiment of the invention the arrays are all located on one large, plane chip-plate, here referred to as the chip carrier plate. The side of this chip plate on which the arrays are located is pressed tightly against the microtitre plate. By inverting this sandwich unit, the arrays are brought into contact with the solutions in the wells, and the primers can be processed.

After the chips have been brought into or onto the wells with the amplified DNA segments, the limited primer extension now begins. The usual temperature cycles of a PCR process cause the single DNA strands to be bonded to the extension primers, and the extension primers are extended by precisely one nucleotide through the operation of a polymerase. Several temperature cycles ensure that the extension, which often does not develop sufficiently in a single cycle, is successful. Since the initial DNA serves as a template for the extension, and the extension primers hybridize immediately next to a mutation site, this terminating nucleotide is a precise indication of the type of the mutation.

After the limited extension of the extension primers bonded to the chip, the chips are washed and freed of all polymerases, buffers, ddNTPs and templates. All the chips on the carrier plate can be washed together, because all of the now extended primers are firmly bonded to the chips. The chips on the carrier plate are then dried and exposed to UV radiation. This radiation cleaves the linkers; the ends of the primers become free. These now free cleavage products, however, carry the information about the mutation site, in a form whose mass is measurable, because the different nucleotides differ by at least 9 and at most 40 atomic mass units. The masses of these cleavage products lie between about 1600 and 1800 atomic mass units. The masses for homozygote A and homozygote B are known precisely each SNP in the genotype profile.

These free cleavage products are now prepared for ionization by matrix assisted laser desorption and ionization (MALDI) by the application of a matrix solution to the individual compartments. The same matrix solution can be applied to all the compartments by micropipetting, using, for instance, piezo or solenoid dispensers. Alternatively, it is possible for the matrix solution to be sprayed on as a fine mist, a process in which the hydrophobic borders between the compartments prevent the samples from becoming mixed. In the subsequent drying process, the cleavage products become locked into the small matrix crystals that form, and are thus prepared for mass spectrometric analysis.

If the carrier plate consists of chips on pillars it is now possible to place an electrically conductive frame over the carrier plate, surrounding the individual chips and contacting them, so that together with the chips it forms the plane, electrically conductive surface required for the generation of an even acceleration field for ion acceleration in laser desorption mass spectrometry. Together with this frame, the carrier plate has the size of a normal microtitre plate. It can be inserted into and analyzed by a mass spectrometer suitable for accepting sample carrier plates that have the size of microtitre plates.

If, on the other hand, the carrier plate is a thin chip plate it can be clamped into a frame that gives it the appropriate size for the mass spectrometer.

The DNA fragments, only a few nucleotides in length, can be analyzed very effectively by MALDI; to record a good quality total spectrum, only 10 individual spectra are needed, generated by 10 laser pulses. Modern mass spectrometers operate with the aid of desorption lasers having a repetition rate of 20 Hertz, and in general capable of continuous operation. This makes it possible to perform the analysis of the samples in the compartments in about one second each. For pentamers, the mass spectra here are only recorded in the mass range between about 1600 and 1800 atomic mass units, and are passed to a transient recorder and to a computation unit for further processing immediately after they have been summed.

In spite of the rapid recording of spectra, the mass spectrometric analysis of the 96 chips, each having 144 samples, and where each of those has 4 multiplexed SNPs, takes about four hours. Together with the sample preparation, which can be completed in about two hours, the measurement of a genotype profile can be completed in one shift. The mass spectrometric measurement can be speeded up by using a lower number of compartments on one chip (for instance, 9 by 9=81 compartments instead of 144 compartments) together with a higher level of multiplexing. Thus a chip with 81 compartments and an 8-fold multiplexed analysis in each compartment 5 yields 648 SNP measurements (or 324 SNP measurements with increased reliability through additional measurement of the complementary strand) and these can be measured in about 2.25 hours.

This is still much too long for urgent analyses. It is therefore appropriate to provide chip carriers with a smaller number of chips for urgent analyses; the preparation of the samples can not be accelerated, but the mass spectrometric analysis can be significantly shortened.

This analysis method is particularly suitable for application with the aid of carefully designed application kits. These application kits must in particular contain the chip carriers for a specific genotyping profile, and the necessary primer pairs for the multiplex PCR amplification of the initial DNA sample.

A kit could also, however, contain the additional chemicals required, such as the NTPs for the amplifying PCR process, the cleaning materials and the mixture of terminating ddNTPs. It would also be possible for the most favorable polymerases for the primary PCR amplification of the templates and for the primer extension as well as purified matrix substances for the MALDI ionization to be included in the kit.

The data for all the masses of the expected fragments and for both alleles in each compartment can also be included on a computer-readable medium. It would even be possible to include an executable computer program that could calculate the medical, breeding-selective or other relevant results according to the latest state of knowledge from the measured genotyping profiles. This program can, for instance, immediately calculate the increased risk of thrombosis of through mutative modification of thrombosis factor V (Leiden allele) or the other thrombosis factors and their interaction.

Finally, it is also possible to combine different genotyping profiles. For instance, a susceptibility profile for an illness can be combined with a profile that provides a genetic pass, and this ensures that patients' samples cannot be mixed up.

While the invention has been shown and described with reference to exemplary embodiments thereof, those skilled in the art will recognize that various changes in form and detail may be made herein without departing from the spirit and scope of the invention as defined by the appended claims.

What is claimed is:

1. Method for mass spectrometric analysis of large numbers of genotyping profiles, the method comprising the steps of:
    (a) providing a sample carrier plate configured to hold a plurality of sample chips mounted in an array on stems or pillars, with each chip carrying DNA probes bonded to the chip surface;
    (b) providing a well plate with a plurality of wells arranged in an array that matches the chip array;
    (c) locating processing liquid in each of the wells;
    (d) contacting the processing liquid of each of the wells with a different one of the chips;
    processing the DNA robes in the processing liquid by chemical or enzymatic reactions;
    (f) locating the sample carrier plate in a mass spectrometer; and
    (g) analyzing products of the reactions by mass spectrometry.

2. Method as in claim 1 wherein the array of wells is part of a microtitre plate.

3. Method as in claim 1 wherein for the mass spectrometric measurement, the chip carrier is embedded in a metallic frame that fills the gaps between the chips, contacts them electrically and forms an even surface with the surfaces of the chips.

4. Method as in claim 3, wherein the chips are fixed on elastic stems on the chip carrier and have an appropriate shape so that their height and separation may be adjusted by a complementary form in the embedding frame.

5. Method as in claim 1 wherein various primers are bonded as the DNA probes in the defined locations on each chip, and wherein the primers are processed together with the amplification products of a DNA sample and supply a genotyping profile for this DNA sample by mass spectrometric analysis.

6. Method as in claim 5 wherein the processing consists in a mutation-dependent primer extension of the various types of bonded primers that function as mutation probes.

7. Method as in claim 5 wherein the primers have cleavable linkers, that these linkers are cleaved prior to the mass spectrometric analysis, and the cleavage fragments are subjected to mass spectrometric analysis.

8. Method as in claim 7 wherein the cleavable linkers are located three, four or five nucleotides from the 3' end.

9. Method as in claim 7 wherein the linkers are photo-cleavable.

10. Method as in claim 1 wherein the samples are ionized for mass spectrometric analysis by laser desorption.

11. Method as in claim 10 wherein the ionization is performed by matrix assisted laser desorption (MALDI).

12. Sample carrier plate for the mass spectrometric analysis of genotyping profiles on individual chips, the sample carrier plate comprising:
    a base plate;
    stems or pillars fixed to a base plate in an array;
    chips fixed to the tops of the stems or pillars; and
    DNA probes bonded to the surfaces of the chips in defined locations.

13. A sample carrier plate as in claim 12 wherein the stems or pillars of the chips are elastic, and wherein the chips each have an appropriate shape that fits into a corresponding opening in an embedding frame.

14. A sample carrier plate as in claim 12 wherein an arrangement of the chip array corresponds to an arrangement of the array of wells in a microtitre plate.

15. A sample carrier plate as in claim 12 wherein each chip contains arrays with primers bonded to the surface as mutation-specific probes for mass spectrometric analysis of a genotyping profile.

16. A sample carrier plate as in claim 15 wherein the primers contain cleavable linkers.

17. A sample carrier plate as in claim 15 wherein all the chips of the chip carrier are prepared for the same genotyping profile.

18. An application kit comprising:
    sample carrier plates according to claim 15; and
    associated mixtures of primer pairs for PCR amplification of the DNA samples in preparation for further processing of the chips for analysis of the genotyping profile.

19. An application kit as in claim 18 wherein the kit also contains the data for the mass spectrometric measurements of the end products of the primers in the compartments and their association with the alleles of the mutations in computer-readable form.

20. An application kit as in claim 18 wherein the kit contains an executable computer program which processes the measured data and presents the genotyping profile.

* * * * *